US008183046B2

(12) United States Patent
Lu et al.

(10) Patent No.: US 8,183,046 B2
(45) Date of Patent: May 22, 2012

(54) TEMPERATURE RESISTANT PH BUFFERS FOR USE AT LOW TEMPERATURES

(75) Inventors: Yi Lu, Champaign, IL (US); Hee-Jung Hwang, Baltimore, MD (US); Nathan Sieracki, Champaign, IL (US); Dewain Garner, Savoy, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 1170 days.

(21) Appl. No.: 11/622,098

(22) Filed: Jan. 11, 2007

(65) Prior Publication Data
US 2008/0171393 A1    Jul. 17, 2008

(51) Int. Cl.
G01N 31/00    (2006.01)
G01N 21/00    (2006.01)
(52) U.S. Cl. ............... 436/18; 436/11; 436/13; 436/16; 435/243; 532/1; 514/1
(58) Field of Classification Search ............ 436/11, 436/13, 16, 18; 435/243; 532/1; 514/1
See application file for complete search history.

(56) References Cited

U.S. PATENT DOCUMENTS
4,915,956 A    4/1990    Alam et al.
6,107,285 A    8/2000    Gatti et al.
6,143,766 A * 11/2000    Kaltenbronn et al. ........ 514/312

OTHER PUBLICATIONS

Bates, R.G. et al., "Dissociation constants of acetic acid and primary phosphate ion and standards for pH in 10, 20, and 40 wt % ethanol/water solvents at 25, 0, -5, and -10° C", Analytical Chemistry, vol. 52, pp. 1598-1601, (1980).
Sigma-Aldrich, BioChemika Ultra, "Biological Buffers", found at http://www.sigmaaldrich.com/Brands/Fluka_Riedel_Home/Bioscience/BioChemika_Ultra/Biological_Buffers.html, pp. 1-24, printed on Sep. 20, 2006.
Chilson, O.P. et al., "Effects of Freezing on Enzymes", Federation proceedings 24, pp. S55-S65, Mar.-Apr. 1965.
Bates, J., "Revised N.B.S. standard buffer solutions for pH measurements from 0° C to 95° C", Data for Biochemical Research, 3$^{rd}$ ed., pp. 421-422, Dawson, R.M.C. et al., Clarendon Press, Oxford, (1986).
Goldberg, R.N. et al., "Thermodynamic quantities for the ionization reactions of buffers", Journal of Physical and Chemical Reference Data, vol. 31, No. 2, pp. 231-370, (2002).
Good, N.E. et al., "Hydrogen ion buffers for biological research", Biochemistry, vol. 5, No. 2, pp. 467-477, (1966).
Good, N.E. et al., "Hydrogen ion buffers", Methods Enzymol., vol. 24, pp. 53-68, (1972).
Hafeman, D.G. et al., "Fundamental thermochromic properties of buffered pH indicator solutions and the formulation of "athermochromic" systems" The Journal of Physical Chemistry, vol. 97, No. 12, pp. 3058-3066, (1993).

(Continued)

*Primary Examiner* — Krishnan S Menon
*Assistant Examiner* — Rebecca M Fritchman
(74) *Attorney, Agent, or Firm* — Klarquist Sparkman, LLP

(57) ABSTRACT

A method for preparing a composition that includes selecting a pH of the composition; selecting a first buffer with a negative temperature coefficient; selecting a second buffer with a positive temperature coefficient; and forming the composition comprising the first buffer and the second buffer. The composition has an average temperature coefficient, $\Delta pH/\Delta T$ $(T_a, T_b) \leq 1 \times 10^{-3}$ pH-unit/K and a $\Delta pH(T_a, T_b) \leq 0.31$ pH-unit for $T_a = 4$ K and $T_b = 313$ K.

15 Claims, 9 Drawing Sheets

OTHER PUBLICATIONS

Hoa, G.H.B. et al., "Ionic strength and protonic activity of supercooled solutions used in experiments with enzyme systems", The Journal of Biological Chemistry, vol. 248, No. 13, pp. 4649-4654, (1973).

Lollar, P. et al., "pH-dependent denaturation of Thrombin-activated porcine factor VIII", The Journal of Biological Chemistry, vol. 265, No. 3, pp. 1688-1692, (1990).

Michelson, S.C., "Dielectric properties of supercooled cryoprotectant agents", Physics in Medicine & Biology, vol. 41, pp. 2053-2066, (1996).

Orii, Y. et al., "Measurement of the pH of frozen buffer solutions by using pH indicators", The Journal of Biochemistry, (Tokyo), vol. 81, pp. 163-168, (1977).

Svistunenko D.A. et al., "The pH dependence of naturally occurring low-spin forms of methaemoglobin and metmyoglobin: an EPR study", Biochemical Journal, vol. 351, pp. 595-605, (2000).

Travers, F. et al., "Dielectric constants of alcoholic-water mixtures at low temperature", The Journal of Physical Chemistry, vol. 74, No. 10, pp. 2243-2244, (1970).

van den Berg, L. et al., "Effect of freezing on the pH and composition of sodium and potassium phosphate solutions; the reciprocal system $KH_2PO_4$-$Na_2$-$HPO_4$-$H_2O^1$", Archives of Biochemistry and Biophysics, vol. 81, pp. 319-329, (1959).

van den Berg, L. et al., "Composition and pH changes during freezing of solutions containing calcium and magnesium phosphate", Cryobiology, vol. 6, Issue 1, pp. 10-14, Jul.-Aug. 1969.

Williams-Smith, D.L. et al., "Changes in apparent pH on freezing aqueous buffer solutions and their relevance to biochemical electron-paramagnetic-resonance spectroscopy", Biochemical Journal, vol. 167, pp. 593-600, (1977).

Finn, D.B., "Denaturation of proteins in muscle juice by freezing", Proceedings of the Royal Society of London. Series B, containing papers of a biological character, vol. B111, pp. 396-411, (1932).

Roy, R.N. et al., "Standard electromotive force of the $H_2$-AgCl;Ag cell in 30, 40, and 50 mass% glycerol/water from -20 to 25° C: $pK_2$ and pH values for a standard "Mops" buffer in 50 mass% glycerol/water", Cryobiology, vol. 22, Issue 6, pp. 578-588, (1985).

Definition of the word "Tartrate" printed from Wikipedia online free encyclopedia (http://en.eikipedia.org/wiki/tartrate) on Sep. 25, 2006.

Roy, R.N. et al., "Thermodynamics of the second dissociation constant and standards for ph of 3-(N-Morpholino) propanesulfonic acid (MOPS) buggers from 5 to 55° C", Journal of Solution Chemistry, vol. 27, No. 1, pp. 73-87, (1998).

\* cited by examiner

A

B

TEMPERATURE RESISTANT PH BUFFERS FOR USE AT LOW TEMPERATURES

FEDERALLY SPONSORED RESEARCH OR DEVELOPMENT

The subject matter of this application may have been funded in part under a research grants from the National Science Foundation (CHE 05-52008) and the National Institutes of Health (GM062211). The U.S. Government may have rights in this invention.

BACKGROUND

Buffer systems are widely used in biology and biochemistry to maintain the pH of solutions. While the pH of a buffered solution resists changes upon the addition of small amounts of an acid or base to the solution, the pH of conventional buffers displays marked temperature dependence. The basis for the observed temperature dependence may be attributed to temperature affecting the ionization of weak acids and bases commonly used in buffer systems, as well as the ionization of water, and/or to the selective precipitation of buffer ions from solution.

Cryogenic temperatures are often required for numerous biochemical and biophysical studies such as the use of electron paramagnetic resonance (EPR), magnetic circular dichroism (MCD), and Mössbauer and X-ray absorption spectroscopy (XAS). In addition, X-ray diffraction data are collected at liquid nitrogen temperatures for protein structure determination. Aqueous buffer solutions are invariably used for these measurements, and low temperatures can change the buffer pH, which in turn, can modify the system inadvertently.

The cryopreservation of biological tissues, cells, and specimens is compromised by thermal fluctuations around the glassing temperature of water (−130° C.; 143 K). Biological and chemical activity can persist as long as water activity exists; however, all activity ceases below 143 K. Even the most temperature-sensitive cells are estimated to survive for hundreds of years when stored at temperatures below 143 K. However, the longevity of cells is reduced to months when stored above this temperature. Since the pH of cryogenic preservative solutions is determined at temperatures far above the glassing temperature of water, significant pH variations are expected as the solutions are subjected to the cryogenic process. Moreover, pH variations will persist whenever variations in temperature arise during long-term storage of cryogenic samples. Temperature dependent pH variation in cryopreservative solutions likely plays a contributory role in the integrity of cryogenic samples.

The stability of pharmaceutical compounds is also affected by temperature dependent pH changes. While solid and lyophilized powder formulations are relatively stable for prolonged periods of time, reconstituted or ready-to-use solutions of pharmaceutical compounds are particularly susceptible to inactivation owing to chemical breakdown over time. Low temperature storage of pharmaceutical solutions under freezing conditions (for example, −20° C. (253 K)) slows the temperature dependent chemical degradation of aqueous formulations. Nevertheless, many pH-sensitive pharmaceutical compounds are adversely affected when solutions containing these ingredients are subjected to repeated cycles of freeze-thaw treatment over time.

The biopharmaceutical industry expends considerable time and resources to develop formulations of pharmaceutical compounds that maintain their activity for prolonged periods of time without low temperature storage. Ready-to-use solution formulations are often preferred for pharmaceutical compounds that are extremely toxic, such as chemotherapeutic agents. The traditional approach to this problem focuses on the development of a ready-to-use solution that circumvents the instability issues peculiar to a chosen pharmaceutical compound for storage at refrigerant temperatures (for example, 4-8° C.). Storage stable, ready-to-use solutions have been achieved for certain pH-sensitive antitumor compounds, such as cisplatin and doxorubicin (Alam et al. 1990; Gatti et al. 2000). No temperature resistant pH buffer systems have been developed that may obviate the need to develop tailored ready-to-use formulations for specific pH-sensitive pharmaceutical compounds.

While it is widely accepted that the pH of buffer solutions changes with temperature, quantitative determination of the pH changes at cryogenic temperatures has not been achieved due to the absence of a suitable probe. Different methods have been used to monitor pH variation as a function of temperature. Measurement of the electromotive force has been used to determine variation of $pK_a$ values of phosphate ion in an ethanol/water mixture at temperatures down to −10° C. (Bates et al. 1980). This method was also used to determine temperature dependence of $pK_a$ of MOPS in a glycerol/water mixture for the temperature range 20 to 25° C. (Roy et al. 1985). Several pH-sensitive dyes have been used to probe the protonic activity of supercooled solutions of water-organic solvent mixtures (Hoa et al. 1973). Similar approaches were used to obtain a rough estimation of the pH changes of selected aqueous buffer solutions upon freezing (Williams-Smith et al. 1977; Orii et al. 1977).

Commonly used pH electrodes have limited utility where pH measurements are performed over a broad temperature range, including extremely low temperatures. A preferred method of measuring pH includes monitoring the optical spectrum of solutions. However, some optical pH-indicators display a temperature dependence that hampers their utility in photometric pH measurements. For example, the spectral properties of the pH-indicators phenol red, bromocresol purple, and bromothymol blue change as a function of both temperature and pH (Hafeman et al. 1993). Buffer/pH-indicator compositions are described for these compounds that display temperature-independent spectral properties for the included pH indicator (id.). It is not clear whether these buffer/pH-indicator compositions can be used to colorimetrically monitor solution pH at different temperatures, owing to the presence of the buffer in the composition. Thus, pH-sensitive dyes whose spectral properties reflect changes in only the pH of the solution are desired.

The temperature effect on pH was originally recognized for low temperature storage of solutions containing proteins. Over seventy years ago, Finn reported that the denaturation of proteins contained in muscle juice was attributed to the variation in hydrogen ion and salt concentrations upon freezing (Finn 1932). Over forty years ago, Chilson and coworkers observed loss of enzymatic activity of aldolase and dehydrogenase in sodium and potassium phosphate buffer solutions upon freezing and thawing, which they attributed to the inactivation of the enzymes by pH changes (Chilson et al. 1965).

More recently, it was recognized that pH-dependent denaturation of proteins can occur by as little as a 1-2 unit variation in pH. For example, thrombin-activated porcine factor VIII is a stable, active, heterotrimer at pH 6.0 at 4° C. or 20° C. However, this protein undergoes a sharp decline in coagulation activity between pH 7 and 8. Furthermore, the coagulation activity of the protein cannot be restored by readjusting the pH to 6.0. The loss of activity correlates with dissociation and precipitation of individual subunits of the trimeric protein. Lollar and Parker (1990) proposed that the denaturation of the protein by pH-dependent subunit dissociation may be a major mechanism for the inactivation of the protein under physiologic conditions.

Thus, subtle variation in solution pH can dramatically alter protein structure and function. The pH of storage solutions for proteins or other pH-sensitive macromolecules can vary dramatically as a function of temperature, thereby affecting their stability.

The problem of buffered solutions displaying marked pH variation as a function of temperature has been long recognized. Yet, surprisingly, there are no published attempts to systematically develop buffer systems that resist temperature dependent variation of pH. Research applications, cryopreservation methodology, and pH-sensitive pharmaceutical compound formulations would certainly benefit from the availability of such buffer systems. Thus, there has been a long felt need for buffer systems that display temperature resistant pH characteristics.

SUMMARY

In a first aspect, the invention is a method for preparing a composition that includes selecting a pH of the composition; selecting a first buffer with a negative temperature coefficient; selecting a second buffer with a positive temperature coefficient; and forming the composition comprising the first buffer and the second buffer. The composition has an average temperature coefficient, $\Delta pH/\Delta T(T_a, T_b) \leq 1 \times 10^{-3}$ pH-unit/K for $T_a = 253$ K and $T_b = 273$ K, or $T_a = 273$ K and $T_b = 293$ K.

In a second aspect, the invention is a solution that includes a first buffer with a negative temperature coefficient and a second buffer with a positive temperature coefficient. The solution has an average temperature coefficient, $\Delta pH/\Delta T(T_a, T_b) \leq 1 \times 10^{-3}$ pH-unit/K for $T_a = 4$ K and $T_b = 313$ K. The solution does not include a pH-indicator dye.

In a third aspect, the invention is a method of preparing a buffer system that includes selecting a first buffer with a negative temperature coefficient; selecting a second buffer with a positive temperature coefficient; and forming a composition comprising the first and second buffers. The buffer system has an average temperature coefficient, $\Delta pH/\Delta T(T_a, T_b) \leq 1 \times 10^{-3}$ pH-unit/K for $T_a = 4$ K and $T_b = 313$ K, a $\Delta pH(4\ K, 313\ K) \leq 0.31$ pH-unit, and a buffering capacity of at least 0.01 for the temperature range of 4 K to 313 K. The buffer system does not include a pH-indicator dye.

In a fourth aspect, the invention is a buffer system that includes a first buffer with a positive temperature coefficient and a second buffer with a negative temperature coefficient. The buffer system has an average temperature coefficient $\Delta pH/\Delta T(T_a, T_b) \leq 1 \times 10^{-3}$ pH-unit/K for $T_a = 4$ K and $T_b = 313$ K, a $\Delta pH(4\ K, 313\ K) \leq 0.31$ pH-unit, and a buffering capacity of at least 0.01 for the temperature range of 4 K to 313 K. The buffer system does not include a pH-indicator dye.

DEFINITIONS

The phrase "weak acid" is a chemical acid that does not fully ionize in aqueous solution; that is, if the acid is represented by the general formula HA, then in aqueous solution A− forms, but a significant amount of undissociated HA still remains. The acid dissociation constant ($K_a$) of a weak acid varies between $1.8 \times 10^{-16}$ and 55.5.

The phrase "weak base" is a base that does not fully ionize in aqueous solution. As bases are proton acceptors, a weak base is defined as a chemical base in which protonation is incomplete; that is, if the base was represented by the general formula B, then in aqueous solution BH+ forms, but a significant amount of unprotonated B still remains. The acid dissociation constant ($K_a$) of the resultant conjugate weak acid BH+ varies between $1.8 \times 10^{-16}$ and 55.5.

The phrase "conjugate acid" is the acid member, HX+, of a pair of two compounds (HX+, X) that transform into each other by gain or loss of a proton.

The phrase "conjugate base" is the base member, X−, of a pair of two compounds (HX, X−) that transform into each other by gain or loss of a proton.

The phrase "conjugate base salt" is the ionic salt comprising a conjugate base, X−, and a positively charged counterion.

The term "buffer" refers to a composition, wherein the composition comprises a weak acid and its conjugate base (usually as a conjugate base salt), or a weak base and its conjugate acid.

The phrase "buffer system" means a mixture containing at least two buffers.

The term "buffering capacity" means the incremental amount of a strong base, measured in equivalents, required to produce a certain pH change of the buffer solution. In mathematical terms, $\beta = \Delta B/\Delta pH$, where $\Delta B$ is the increment (in equivalents) of a strong base and $\Delta pH$ is the change in pH. Strong acids effect negative increment ($-\Delta B$) and lower the pH.

The term "$pH_{max}(T_a, T_b)$" means the highest pH measured for the range defined by temperature $T_a$ and temperature $T_b$.

The term "$pH_{min}(T_a, T_b)$" means the lowest pH measured for the range defined by temperature $T_a$ and temperature $T_b$.

The term "$\Delta pH(T_a, T_b)$" means the absolute change in pH between the highest pH and the lowest pH measured for the range defined by temperature $T_a$ and temperature $T_b$. In mathematical terms, $\Delta pH(T_a, T_b) = pH_{max}(T_a, T_b) - pH_{min}(T_a, T_b)$.

The term "temperature coefficient" means a change of pH value per change in unit temperature ($\Delta pH/\Delta T$). It can be positive or negative. Unit temperature is specified as Kelvins.

The term "average temperature coefficient," $\Delta pH/\Delta T(T_a, T_b)$, is defined as $[\Delta pH(T_a, T_b)]/(T_a - T_b)$ for the temperature range bounded by temperature $T_a$ and temperature $T_b$.

The term "pH indicator," as used herein, refers to a compound that displays a spectral property that depends upon the pH of the solution containing the compound. An example of a pH indicator is a pH indicator dye (or pH-sensitive indicator dye), such as phenol red, bromocresol purple, bromothymol blue, and bromocresol green, among others, and mixtures thereof.

DETAILED DESCRIPTION

The present invention makes use of the discovery that temperature resistant pH solutions and buffer systems may be created by combining two or more buffers, where the buffers have opposite temperature coefficients in the same temperature range. The resultant compositions display a negligible temperature coefficient over a wide range of temperature, including cryogenic temperatures. In addition, it has also been discovered that changes in the optical spectrum of solutions containing pH-sensitive indicator dyes permit indirect measurement of solution pH at low temperatures. These reagents enable one to systematically explore the pH-temperature profiles for a variety of solutions and buffer systems over an extraordinarily wide range of temperatures (for example, 70-370 K) and to rapidly evaluate buffer combinations as temperature resistant pH solutions and buffer systems. These solutions and buffer systems, as well as the methods for their identification and preparation, satisfy a long-felt need with regard to developing temperature resistant pH buffers for use in biochemical, biophysical, and pharmaceutical applications.

The pH-sensitive indicator dyes have utility in identifying compositions that have temperature resistant pH properties over a selected temperature range. Once such compositions are identified, however, compositions that do not contain pH indicator dyes are prepared and used. For example, compositions that are suitable for biochemical, biophysical, and pharmaceutical applications will not contain a pH indicator dye. Exclusion of the pH indicator dyes is particularly important for pharmaceutical compositions, owing to the potential toxicity of these dyes.

Measuring pH as a function of temperature employs a pH-sensitive calorimetric dye system. Preferably, the spectral properties of the dye are negligibly affected by temperature. Even more preferably, the pH-sensitive dye does not alter the pH properties of the buffered solutions. Most preferably, the pH-sensitive dye does not appreciably interact with components of the solution, including buffering species, additional ions or electrolytes, and any compounds present in solution.

Although a pH-sensitive dye having a single absorption band in the visible region may be used in the colorimetric determination of pH, interference owing to baseline shift at low temperatures may confound such measurements. Therefore, use of indicators that have two distinct absorption bands in the visible region and over a broad range of pH is preferred for ratiometric and colorimetric determination of the pH of solutions. Even more preferably, and for quantitative purposes, the two absorption peaks having a ratio between 10 and 0.1 is desired for accurate ratiometric determinations. Most preferably, the absorption maxima should be sufficiently well resolved to permit accurate colorimetric determination of the individual peaks.

Figure 1:
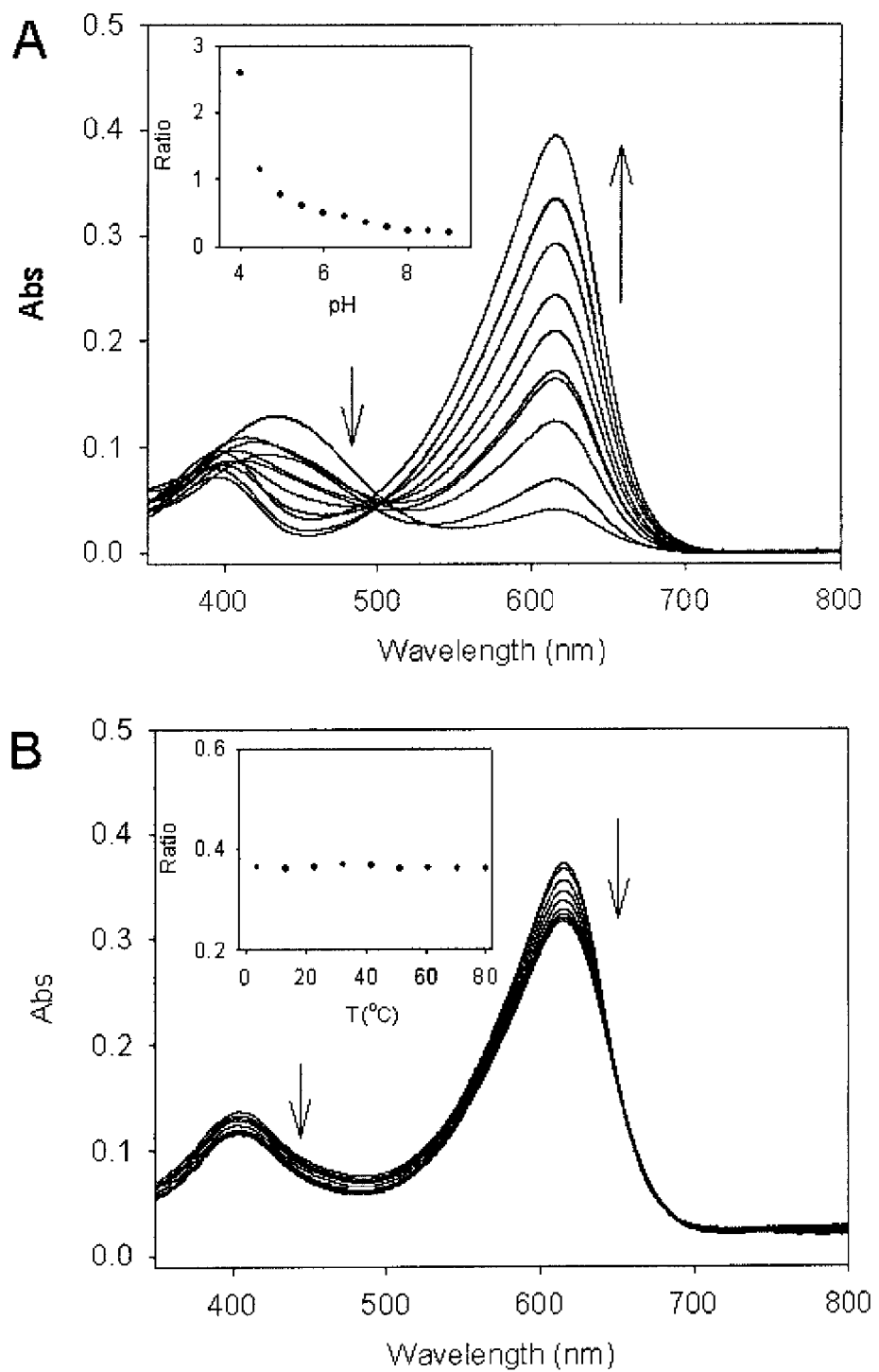
FIG. 1(A) depicts UV-vis spectra of 1 v/v % indicator 1 solution of 50 mM mixed buffer (50 mM sodium acetate, 50 mM 3-Morpholinopropanesulfonate (MOPS), 50 mM Tris Hydroxymethylaminoethane (Tris) at various pH values. The arrows indicate the direction of absorbance change as a function of increasing pH. The inset depicts the ratio of $A_{418}/A_{623}$ as a function of pH.
FIG. 1(B) depicts temperature dependent spectral changes of 1 v/v % of indicator 1 in water. The arrows indicate the direction of absorbance change as a function of increasing temperature. The inset depicts the ratio of two absorption peaks ($A_{418}/A_{623}$) as a function of temperature.

Examples of two pH-sensitive dyes that meet these criteria include bromocresol green and bromothymol blue. Bromocresol green displays a pKa of 4.6, and bromothymol blue displays a pKa of 7.1. Both dyes are yellow in their acidic form and blue in their basic form. An especially preferred pH-sensitive indicator is a mixture of bromocresol green and bromothymol blue (indicator 1). FIG. 1(A) depicts the optical spectrum of indicator 1, showing two absorption peaks around ~420 nm and ~620 nm. The inset of FIG. 1(A) illustrates that the intensity ratio of these two absorption peaks varies from 3 to 0.2 as a function of pH. FIG. 1(B) illustrates that for the temperature range 4° C. to 80° C., the ratio of the two absorption peaks remains constant. Indicator 1 is a preferred pH-sensitive dye indicator system because the spectral changes of the solution are attributed to the protonation state of the dyes resulting from changes in the pH of the solution.

Preferred solutions for performing ratiometric determinations of pH include indicator 1 dissolved in an aqueous solution. An especially preferred concentration of indicator 1 is 1% by weight.

The temperature resistant pH solutions of the present invention are identified by evaluating a series of solutions that contain indicator 1, and different concentration ratios of two buffers having opposite temperature coefficients. Examples of a preferred first buffer having a negative temperature coefficient include phthalate, acetate, MOPS, Tris, 2-[bis(2-hydroxyethyl)amino]-2-(hydroxymethyl)propane-1,3-diol (BisTris), BisTrisPropane (BTP), 2-Morpholinoethanesulfonic (MES), and HEPES, and their corresponding conjugate acid and base salt forms. Examples of a preferred second buffer having a positive temperature coefficient include phosphate, tartrate, and borate, and their corresponding conjugate acid and base salt forms (Bates, 1962; Dawson et al., 1986).

A solution series containing buffer components and indicator 1 is prepared and adjusted to a specific pH at room temperature. Optionally, a glassing agent, such as glycerol, can be included in the solutions. Aliquots of the solutions are equilibrated at different temperatures, and the optical spectrum of each solution is recorded. The ratio of the two absorption peaks ($A_{418}/A_{623}$) at each temperature is converted to a pH value using an absorption-pH calibration curve established for indicator 1 at room temperature. Optionally, a plot of pH versus temperature is prepared to visualize the relationship.

Figure 2:
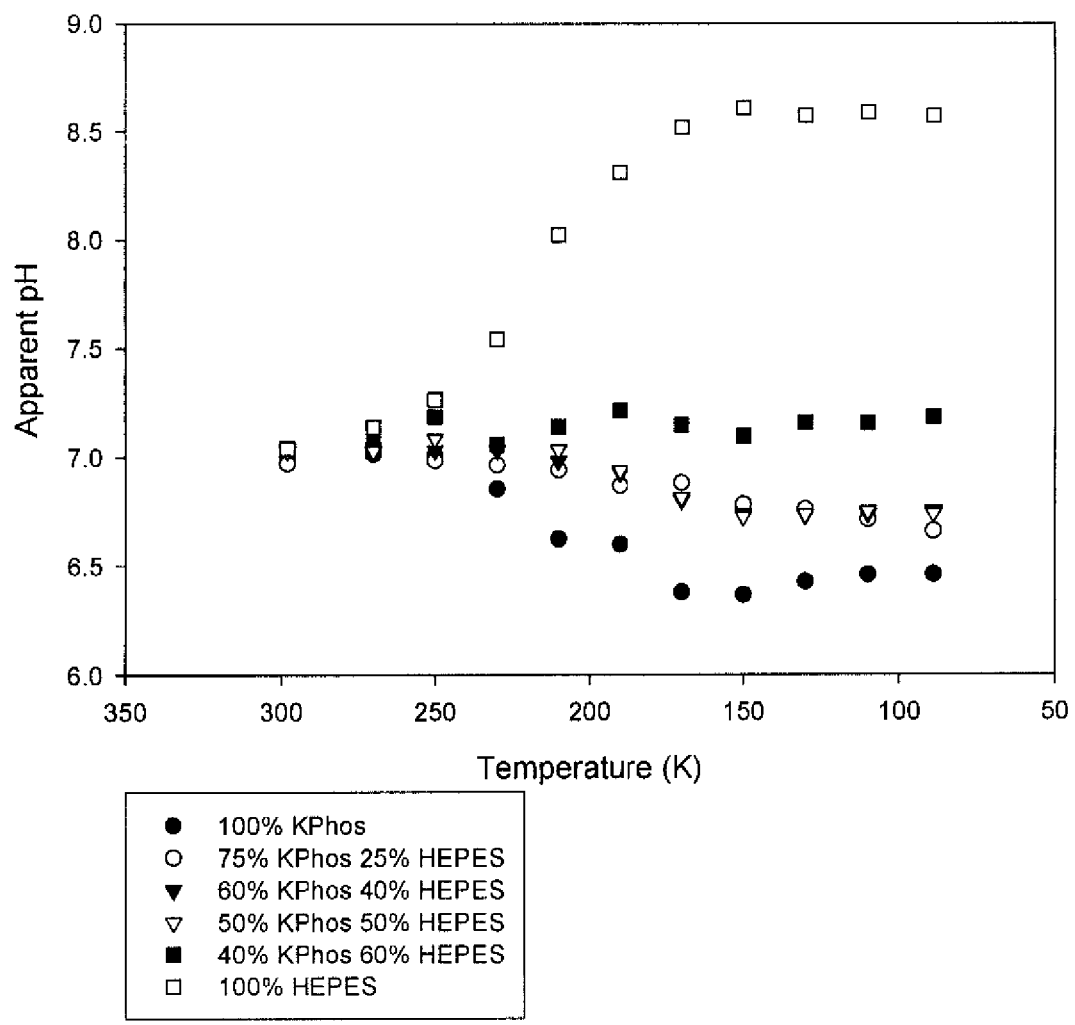
FIG. 2 depicts the temperature dependence of pH of 75% glycerol solutions containing 4-(2-hydroxyethyl)-1-piperazineethanesulfonate (HEPES) buffer and potassium phosphate (KPhosphate) buffer, or mixtures thereof.

As shown in FIG. 2, HEPES-potassium phosphate (KPhosphate) mixtures display a greater resistance to change in pH as a function of temperature than solutions containing either HEPES or KPhosphate alone. Since the ΔpH of a 50 mM HEPES-buffered solution between 298 K and 150 K was about 3-fold greater than a 50 mM KPhosphate-buffered solution adjusted to pH 7.0 (Table 1), one might have expected that a buffered solution containing a 3-fold greater concentration of KPhosphate relative to HEPES would provide a temperature resistant pH buffer. However, this buffer composition (HEPES:KPhosphate (25:75)) displayed a ΔpH of −0.34 over a 208 K range (298 K to 90 K), which is similar to the ΔpH of −0.50 observed for the KPhosphate-buffered solution (Table 1). A 50 mM buffer solution containing 30 mM HEPES and 20 mM KPhosphate provides a ΔpH of +0.09 over the 208 K range (Table 1; (HEPES:KPhosphate (60:40)) indicating that this buffer system displays a temperature coefficient of ~+4.3×10$^{-4}$ pH-unit/K. Thus, a series of solutions containing different ratios of buffers are empirically evaluated to ascertain buffer systems having a ΔpH ($T_a$, $T_b$) indicative of a temperature resistant pH solution.

Figure 3:
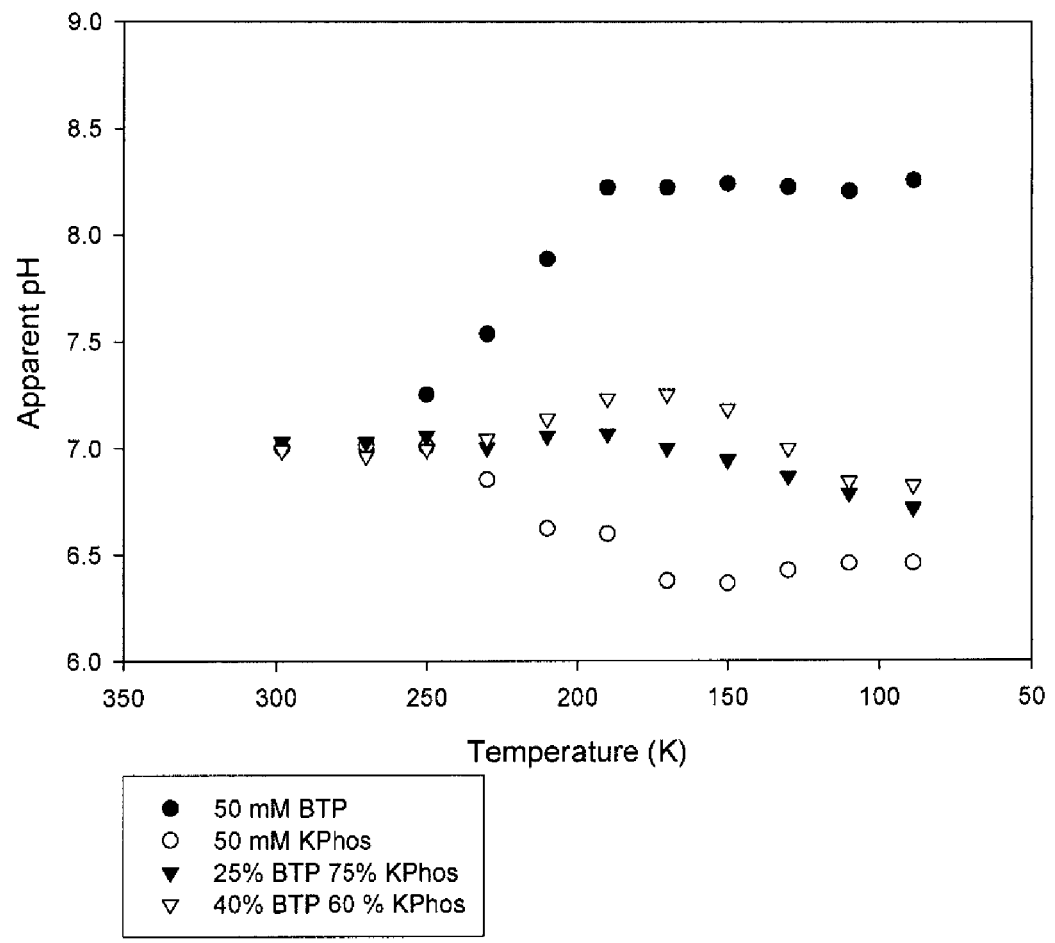
FIG. 3 depicts the temperature dependence of pH of 75% glycerol solutions containing BisTris Propane (BTP) buffer and KPhosphate buffer, or mixtures thereof.

A detailed empirical analysis of the solution series over different temperature ranges enables one to identify temperature resistant pH solutions having preferred ΔpH($T_a$, $T_b$) values. For example, mixtures of BTP-KPhosphate display smaller ΔpH values (for example, 0.18 pH-unit and 0.29 pH-unit) over the 208 K range relative to the single buffer solutions (FIG. 3; Table 1). Thus, solutions containing these buffer mixtures are temperature resistant pH solutions. However, at temperatures below 200 K, the ΔpH of a solution containing 20 mM BTP and 30 mM KPhosphate (BTP-KPhosphate (40:60)) displays unusual characteristics: this solution displays a positive ΔpH in the range from 230 K to 170 K and a negative ΔpH below 170 K (FIG. 3). This trend was partially suppressed for a solution containing 12.5 mM BTP and 37.5 mM KPhosphate (BTP-KPhosphate (25:75)), where the only deviation from pH 7.0 is a negative ΔpH trend at temperatures below 170 K (FIG. 3). The BTP-KPhosphate (25:75) solution behaves as an especially preferred temperature resistant pH solution over the temperature range 298 K to 170 K (FIG. 3), displaying a ΔpH of ~0.03 pH-unit and a temperature coefficient of ~+2.3×10$^{-4}$ pH-unit/K.

TABLE 1

Summary of temperature dependence of pH for different buffer compositions

| Buffer System[1] | Ratio[2] | pH at 298 K | pH at plateau[3] | ΔpH |
|---|---|---|---|---|
| HEPES:KPhosphate | 0:100 | 7.0 | 6.5 | −0.50 |
| HEPES:KPhosphate | 25:75 | 7.0 | 6.66 | −0.34 |
| HEPES:KPhosphate | 40:60 | 7.0 | 6.74 | −0.26 |
| HEPES:KPhosphate | 50:50 | 7.0 | 6.73 | −0.27 |
| HEPES:KPhosphate | 60:40 | 7.0 | 7.09 | +0.09 |
| HEPES:KPhosphate | 100:0 | 7.0 | 8.5 | +1.50 |
| BTP:KPhosphate | 0:100 | 7.0 | 6.5 | −0.50 |
| BTP:KPhosphate | 25:75 | 7.0 | 6.71 | −0.29 |
| BTP:KPhosphate | 40:60 | 7.0 | 6.82 | −0.18 |

[1]Total buffer concentration, 50 mM;
[2]Percentage composition of the respective buffers;
[3]Averaged pH values, as measured at plateau between temperatures 150 K to 90 K.

The precise concentration ratio of two buffers for achieving a temperature resistant pH solution is empirically determined by evaluating the pH-temperature profiles for a series of buffer combinations, like that described for the HEPES/KPhosphate and BTP/KPhosphate buffer systems. For a buffer system that includes buffers A and B, where A and B have opposite temperature coefficients in the same temperature range, the preferred series of combinations of A and B that may be prepared and evaluated includes the range of buffer concentration ratios of A:B, such as from 1:99 to 99:1, including 5:95, 10:90, 15:85, 20:80, 25:75, 30:70, 35:65, 40:60, 45:55, 50:50, 55:45, 60:40, 65:35, 70:30, 75:25, 80:20, 85:15, 90:10, and 95:5. In this example, other ranges of buffer concentration ratios of A:B are possible, such as from 0.5:99.5 to 99.5:0.5, from 0.1:99.9 to 99.9:0.1, and the like. The buffer ratios represent the percent mole fraction of each buffer species present in the final buffer system. For example, a 50 mM buffer system that includes buffers A and B having an A:B ratio of 35:65, the final concentrations of buffers A and B in the buffer system will be 17.5 mM and 32.5 mM, respectively.

The preferred buffer system will be the composition of the series that displays the smallest change of pH as a function of temperature for a defined temperature range. Preferred solutions and buffer systems have a ΔpH($T_a$, $T_b$) no greater than 0.02 pH-unit for the temperature ranges 253 K to 273 K and 273 K to 293 K; a ΔpH($T_a$, $T_b$) no greater than 0.04 pH-unit for the temperature ranges 253 K to 293 K and 273 K to 313 K; a ΔpH($T_a$, $T_b$) no greater than 0.06 pH-unit for the temperature range 253 K to 313 K; a ΔpH($T_a$, $T_b$) no greater than 0.11 pH-unit for the temperature range 203 K to 313 K; a ΔpH($T_a$, $T_b$) no greater than 0.12 pH-unit for the temperature range 193 K to 313 K; a ΔpH($T_a$, $T_b$) no greater than 0.17 pH-unit for the temperature range 143 K to 313 K; a ΔpH($T_a$, $T_b$) no greater than 0.22 pH-unit for the temperature range 90 K to 313 K; and a ΔpH($T_a$, $T_b$) no greater than 0.31 pH-unit for the temperature range 4 K to 313 K. For any chosen temperature range, the preferred solutions and buffer systems will have a temperature coefficient in the range from 1.0×10$^{-5}$ pH-unit/K to 1.0×10$^{-3}$ pH-unit/K, including 1.0×10$^{-5}$ pH-unit/K, 2.5×10$^{-5}$ pH-unit/K, 5.0×10$^{-5}$ pH-unit/K, 7.5×10$^{-5}$ pH-unit/K, 1.0×10$^{-4}$ pH-unit/K, 2.5×10$^{-4}$ pH-unit/K, 5.0×10$^{-4}$ pH-unit/K, 7.5×10$^{-4}$ pH-unit/K, and 1.0×10$^{-3}$ pH-unit/K.

The preferred solutions and buffer systems have a temperature resistant pH for the temperature range spanning 4 K to 370 K. More preferably, the solutions and buffer systems have a temperature resistant pH for the temperature ranges spanning 90 K to 313 K, including 253 K to 273 K; 253 K to 293 K; 253 K to 313 K; 273 K to 293 K; 273 K to 313 K; 203 K to 313 K; 193 K to 313; and 143 K to 313 K. Even more preferably, the solutions and buffer systems have a temperature resistant pH for the temperature range spanning 90 K to 313 K, including 100 K, 110 K, 120 K, 130 K, 140 K, 143 K, 150 K, 160 K, 170 K, 180 K, 183 K, 190 K, 193 K, 200 K, 203 K, 210 K, 220 K, 230 K, 240 K, 250 K, 253 K, 260 K, 270 K, and 298 K.

A temperature resistant pH solution or buffer system displays a minimum ΔpH($T_a$, $T_b$) for a given temperature range. For example, a preferred BTP/KPhosphate composition displays a ΔpH (90 K, 298 K) of 0.34 pH-unit. However, this composition has a smaller ΔpH (170 K, 298 K) of ~0.03 pH-unit. Thus, preferred solutions and buffer systems can be characterized as having a minimum ΔpH($T_a$, $T_b$) for a given temperature range.

Buffers suitable for use in the present invention include all biochemically and physiologically acceptable buffers known in the art, including those listed in Table 2. The preferred concentration of buffers is within the range of 1 mM to 500 mM, including 1 mM, 5 mM, 10 mM, 25 mM, 50 mM, 75 mM, 100 mM, 150 mM, 200 mM, 300 mM, 400 mM and 500 mM. An especially preferred concentration of buffer is 50 mM. Preferably, the buffer may be prepared using a weak acid and a conjugate base salt, or a weak base and a conjugate acid salt. Optionally, the pH of the buffer may be adjusted with any acid or base known in the art, including strong mineral acids, such as hydrochloric, hydrobromic, sulfuric, phosphoric, nitric and the like, and bases, such as potassium hydroxide or sodium hydroxide.

TABLE 2 pKa Value and Buffer Range of important Biological Buffers[1]

| Buffer | pK$_a$ at 25° C. | Effective pH Range |
|---|---|---|
| ACES | 6.78 | 6.1–7.5 |
| acetate | 4.76 | 3.6–5.6 |
| ADA | 6.59 | 6.0–7.2 |
| ammonium hydroxide | 9.25 | 8.8–9.9 |
| AMP (2-amino-2-methyl-1-propanol) | 9.69 | 8.7–10.4 |
| AMPD (2-amino-2-methyl-1,3-propanediol) | 8.80 | 7.8–9.7 |
| AMPSO | 9.00 | 8.3–9.7 |
| BES | 7.09 | 6.4–7.8 |
| BICINE | 8.26 | 7.6–9.0 |
| bis-tris | 6.46 | 5.8–7.2 |
| BIS-TRIS propane (BTP) | 6.80, 9.00 | 6.3–9.5 |
| borate | 9.23, 12.74, 13.80 | 8.5–10.2 |
| CABS | 10.70 | 10.0–11.4 |
| cacodylate | 6.27 | 5.0–7.4 |
| CAPS | 10.40 | 9.7–11.1 |
| CAPSO | 9.60 | 8.9–10.3 |
| carbonate (pK1) | 6.35 | 6.0–8.0 |
| carbonate (pK2) | 10.33 | 9.5–11.1 |
| CHES | 9.50 | 8.6–10.0 |
| citrate (pK1) | 3.13 | 2.2–6.5 |
| citrate (pK2) | 4.76 | 3.0–6.2 |
| citrate (pK3) | 6.40 | 5.5–7.2 |
| DIPSO | 7.52 | 7.0–8.2 |
| EPPS, HEPPS | 8.00 | 7.6–8.6 |
| ethanolamine | 9.50 | 6.0–12.0 |
| formate | 3.75 | 3.0–4.5 |
| glycine (pK1) | 2.35 | 2.2–3.6 |
| glycine (pK2) | 9.78 | 8.8–10.6 |
| glycylglycine (pK1) | 3.14 | 2.5–3.8 |
| glycylglycine (pK2) | 8.25 | 7.5–8.9 |
| HEPBS | 8.30 | 7.6–9.0 |
| HEPES | 7.48 | 6.8–8.2 |
| HEPPSO | 7.85 | 7.1–8.5 |
| histidine | 1.70, 6.04, 9.09 | 5.5–7.4 |
| hydrazine | 8.10 | 7.5–10.0 |
| imidazole | 6.95 | 6.2–7.8 |
| malate (pK1) | 3.40 | 2.7–4.2 |
| malate (pK2) | 5.13 | 4.0–6.0 |
| maleate (pK1) | 1.97 | 1.2–2.6 |
| maleate (pK2) | 6.24 | 5.5–7.2 |
| MES | 6.10 | 5.5–6.7 |
| methylamine | 10.66 | 9.5–11.5 |
| MOBS | 7.60 | 6.9–8.3 |
| MOPS | 7.14 | 6.5–7.9 |
| MOPSO | 6.87 | 6.2–7.6 |
| phosphate (pK1) | 2.15 | 1.7–2.9 |
| phosphate (pK2) | 7.20 | 5.8–8.0 |
| phosphate (pK3) | 12.33 | 11.5–13.0 |
| phthalate (pK1) | 2.95 | 2.5–3.8 |
| phthalate (pK1) | 5.41 | 4.5–6.3 |
| piperazine (pK1) | 5.33 | 5.0–6.0 |
| piperazine (pK2) | 9.73 | 9.5–9.8 |
| piperidine | 11.12 | 10.5–12.0 |
| PIPES | 6.76 | 6.1–7.5 |
| POPSO | 7.78 | 7.2–8.5 |
| propionate | 4.87 | 3.8–5.6 |
| pyridine | 5.23 | 4.9–5.9 |
| pyrophosphate | 0.91, 2.10, 6.70, 9.32 | 7.0–9.0 |
| succinate (pK1) | 4.21 | 3.2–5.2 |
| succinate (pK2) | 5.64 | 5.5–6.5 |
| TABS | 8.90 | 8.2–9.6 |
| TAPS | 8.40 | 7.7–9.1 |
| TAPSO | 7.61 | 7.0–8.2 |
| Tartrate | 3.00, 4.40 | 2.5–5.0 |
| taurine (AES) | 9.06 | 8.4–9.6 |
| TES | 7.40 | 6.8–8.2 |
| tricine | 8.05 | 7.4–8.8 |
| triethanolamine (TEA) | 7.76 | 7.0–8.3 |
| Trizma (tris) | 8.06 | 7.5–9.0 |

[1]Adapted from http://www.sigmaaldrich.com/Brands/Fluka_Riedel_Home/Bioscience/BioChemika_Ultra/Biological_Buffers.html The temperature coefficient over a desired temperature range for a buffer can be characterized simply and quickly. For example, establishing whether a particular buffer displays a positive or negative temperature coefficient over a given temperature range can be empirically determined following three simple steps, all of which can be accomplished in a small amount of laboratory time (for example, about sixty minutes): a solution is prepared containing indicator 1, optionally a glassing agent, such as glycerol, and a buffer adjusted to a particular pH at a given temperature; aliquots of the solution are equilibrated at two or more different temperatures (for example, 298 K and 253 K); and the optical properties of indicator 1 are recorded using a spectrophotometer. Because the ratiometric and colorimetric properties of indicator 1 correlate only with solution pH, one can readily ascertain whether the buffer displays a positive or negative temperature coefficient by determining the $A_{418}/A_{623}$ ratio for the solution equilibrated at two different temperatures.

Figure 4:
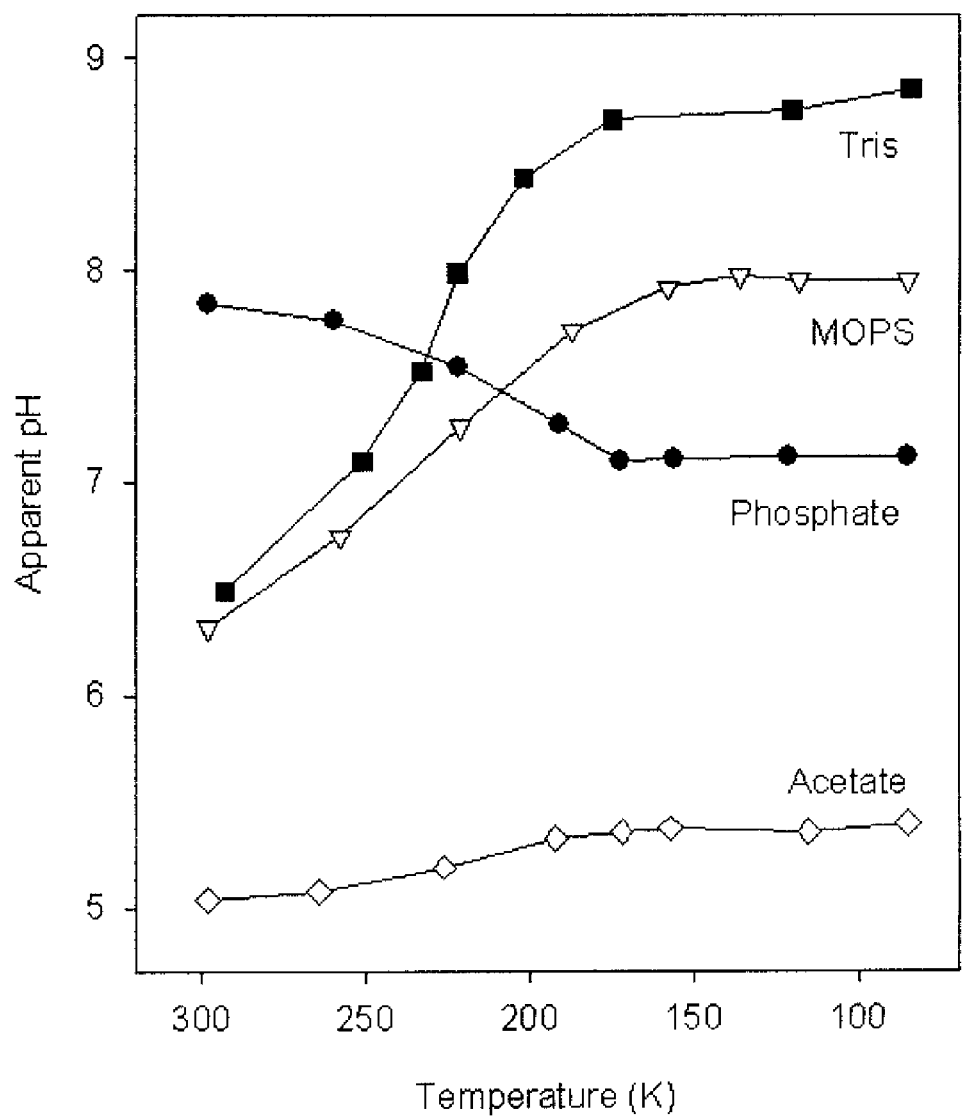
FIG. 4 depicts the temperature dependence of pH of selected 50 mM buffer solutions containing 75% glycerol.

FIG. 4 illustrates a representative plot of this relationship for four different buffers prepared at different pH values. The pH of solutions buffered by Tris, MOPS, or acetate increases as the solution is equilibrated at lower temperatures. By contrast, the pH of a solution buffered by KPhosphate decreases as the solution is equilibrated at lower temperatures. Table 3 summarizes the change in pH ($\Delta$pH) as a function of decreasing temperature for seven solutions prepared with different buffers and pH values. The observed trends in $\Delta$pH correlate with the identity of the buffer present in solution rather than with the pH of the solution. Thus, a solution of a buffer having a negative temperature coefficient increases in pH at decreasing temperatures, whereas a solution of a buffer having a positive temperature coefficient decreases in pH at decreasing temperatures. In general, most buffers have a negative temperature coefficient.

TABLE 3

Summary of temperature dependence of pH for different buffers

| Buffer | pH at 298 K | pH at plateau[1] | $\Delta$pH[2] |
|---|---|---|---|
| KPhosphate | 8.0 | 7.3 | −0.7 |
| KPhosphate | 7.0 | 6.5 | −0.5 |
| Na-Acetate | 5.0 | 5.4 | +0.4 |
| MOPS | 6.1 | 7.7 | +1.6 |
| Tris | 7.0 | 9.2 | +2.2 |
| BisTris | 6.0 | 8.1 | +2.1 |
| BisTrisPropane (BTP) | 6.1 | 8.2 | +2.1 |
| MES | 6.0 | 7.4 | +1.4 |
| HEPES | 6.3 | 7.6 | +1.3 |
| HEPES | 7.0 | 8.5 | +1.5 |

[1]Averaged pH values, as measured at plateau between temperatures 150 K to 90 K.
[2]The $\Delta$pH reported reflects the change in pH as a function of decreasing temperature.

Additional guidance regarding the selection of a buffer having a positive or negative temperature coefficient may be provided by evaluating compositions that include a selected buffer with a suitable concentration of a pH-indicator whose spectral properties displays a marked temperature dependence. For example, two buffers having opposite temperature coefficients can be inferred after determining that their thermochomicities with the pH-indicator phenol red are of opposite sign. These buffers may then be selected and analyzed with indicator 1 to ascertain the appropriate molar composition of each buffer that provides for a temperature resistant pH independent solution or buffer system. The determination of the thermochomatic properties of solutions containing phenol red or other temperature-dependent pH indicators is possible according to the method of described in D. G. Hafeman et al., "Fundamental thermochromic properties of buffered pH indicator solutions and the formation of "athermochromic" systems" J. Phys. Chem. 97:3058-66 (1993), which is hereby incorporated by reference in its entirety.

The development of a set of temperature resistant pH solutions and buffer systems that span the biochemically and physiologically useful pH values for different temperature ranges can be prepared. Owing to the diverse range of pKa values covered by buffers, temperature resistant pH solutions and buffer systems are possible that span a wide range of pH values, such as from pH 2 to 12. Preferred buffer systems will afford a buffering capacity in the physiologically acceptable range from pH 3 to pH 10, such as pH 5, 6, 7, and 8. Examples of possible temperature resistant pH buffer systems spanning this range are shown in Table 4.

TABLE 4

Candidate temperature resistant pH buffer systems

| Buffer System | Effective pH Range |
| --- | --- |
| KPhosphate-KPhthalate | 2.0–3.8 |
| NaTartrate-NaAcetate | 3.5–5.6 |
| MES-KPhosphate | 5.2–8.1 |
| NaTRIS-NaBorate | 7.2–9.0 |
| BisTrisPropane-NaBorate | 8.3–10.0 |

Temperature resistant pH buffer systems can be designed having a specific absolute apparent temperature coefficient and a buffering capacity over a preferred pH and temperature range. Since each buffer system has a unique set of chemical attributes (identity of the buffering species; concentration of the buffering species; absolute apparent temperature coefficient; buffering capacity effective for a given pH range; and preferred temperature range), numerous temperature resistant pH solutions suitable to a variety of biophysical, biochemical, and pharmaceutical applications can be prepared. Additional guidance with the determination of buffering capacity for a given solution is provided by the theoretical framework of Hafeman et al. (1993).

In addition to two-buffer systems, more complex temperature resistant pH buffer systems are possible. For example, systems that include three, four and five buffers can be prepared.

EXAMPLES

Example 1

Buffer Preparation

Dipotassium hydrogenphosphate (Fisher Scientific), Monopotassium hydrogenphosphate (Fisher Scientific), MOPS (3-N-morpholino propansulfonic acid) (Fisher Scientific), sodium acetate (Fisher Scientific), Tris (2-Amino-2-(hydroxymethyl)-1,3-propanediol) (Fisher Scientific), Bis-Tris (2-bis(2-hydroxyethyl)amino-2-(hydroxymethyl)-1,3-propanediol) (Fisher Scientific), BisTris Propane (1,3-bis[tris(hydroxymethyl)methylamino]propane) (Fisher Scientific), MES (2-morpholinoethanesulfonic acid), glycerol (Fisher Scientific), and DTPA (diethylenetriaminepentaacetic acid) (Sigma-Aldrich) were used as purchased.

Sodium acetate buffer solution was made from desired amount of sodium acetate and acetic acid calculated from Henderson-Hasselbalch equation. Potassium phosphate buffer was made likewise from $KH_2PO_4$ and $K_2HPO_4$. MOPS and MES buffers were made from zwitterionic form and desired pH was achieved by adding KOH. TRIS, BisTris, and BTP buffer were prepared similarly, and the pH was adjusted by adding HCl. Mixed buffer solution of pH from 4.0 to 9.0 (50 mM sodium acetate, 50 mM MOPS, 50 mM potassium phosphate, 50 mM Tris) was used for testing the pH-sensitivity of indicator solution over a wide pH range.

Example 2 pH-Sensitive Indicator Dyes

Bromothymol Blue (BTB) (Fisher Scientific) and Bromocresol Green (BCG) (Acros, N.J.) were used without further purification. Indicator 1 solution was prepared with 0.075% (w/w) BTB, 0.075% (w/w) BCG in 70% 2-propanol and 30% water mixture.

For the measurement of the spectral changes of indicator 1 solution containing pure water at high temperature, deionized water from a Milli-Q® Plus PF system (Millipore, Bedford, Mass.) was boiled to remove carbonate and cooled down under argon. Sodium chloride was added the water to the final concentration of 50 mM in order to match the ionic strength of the buffer.

Example 3

Calibration Curves for pH Measurements

To determine the pH of the buffers at low temperature, a calibration curve was made for each buffer at appropriate pH range. After addition of 75 v/v % glycerol, the pH of the buffer solution containing 1 v/v % the indicator 1 solution was measured and the optical spectra were recorded at room temperature as reference data. Final concentration of buffer solutions kept constant at 50 mM. The pH of the buffer solution did not change upon addition of pH indicators.

Example 4

UV-vis Spectrometer for Variable Temperature Studies

In order to measure UV-vis spectra at low temperature, Cary 3E UV-vis (Varian, Palo Alto, Calif.) spectrometer was modified with a transparent double-Dewar system. The transparent disposable cuvette (Fisher Scientific) with path length 4.3 mm was inserted and stabilized in the inner Dewar. The thermometer rod was attached at the corner of the cuvette in order to measure the temperature of cuvette directly. In order to control the temperature, liquid $N_2$ was poured through the plastic funnel, which is connected with long and thin tube down the Dewar. To avoid condensation outside of the Dewar, stream of air was blown to the Dewar throughout the experiments. The control of temperature was achieved by the amount of liquid $N_2$ in the Dewar and the temperature was monitored with a digital thermometer (Digi-sense, Cole Parmer). The pH measurements at room temperature were made using an Accumet AB15 pH meter (Fisher Scientific).

Example 5

Temperature Dependent pH Effects on MOPS Buffer

Figure 5:
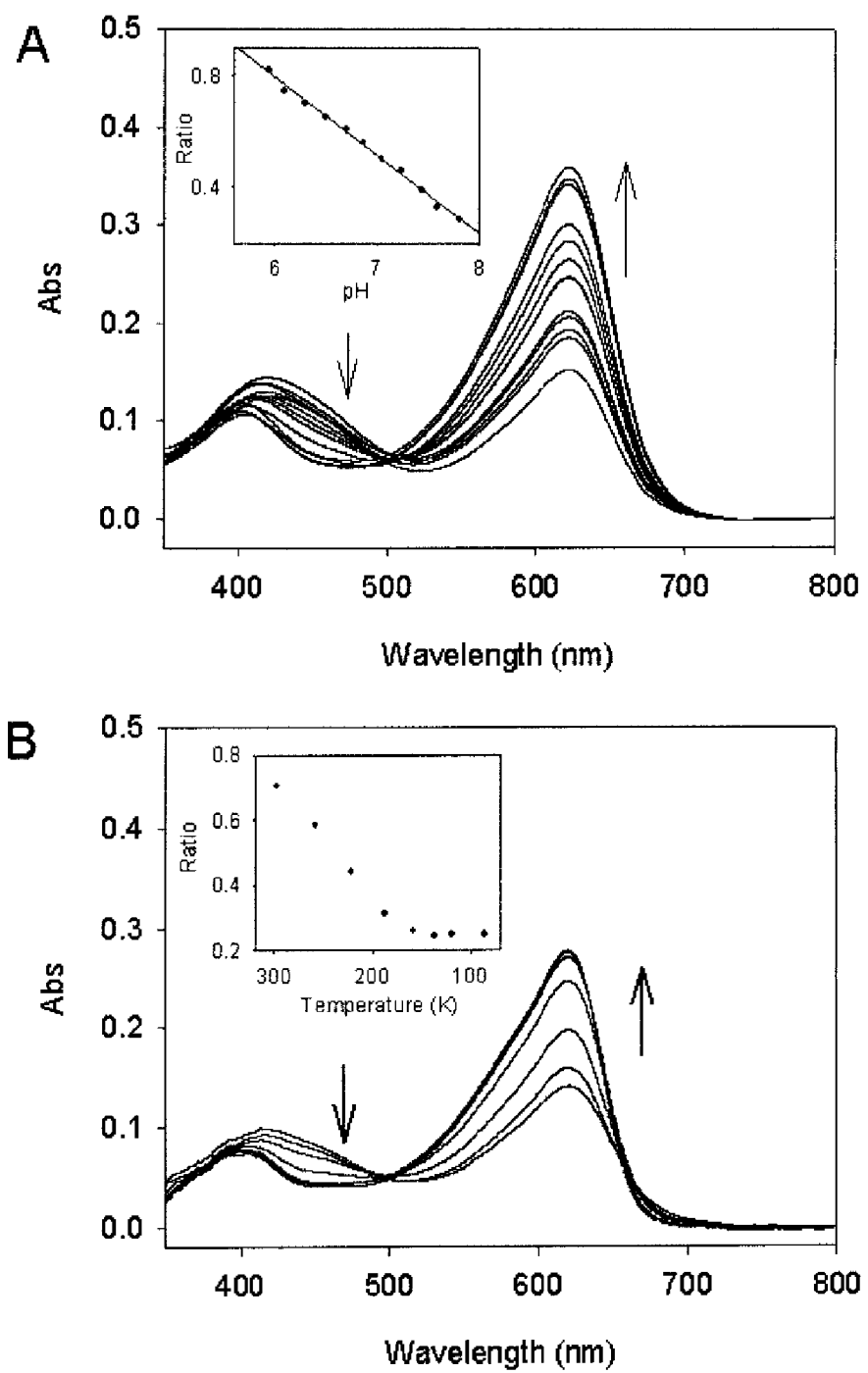
FIG. 5(A) depicts spectral changes of 1 v/v % of indicator 1 solution of 50 mM MOPS buffer containing 75% glycerol at various pH values. The arrows indicate the direction of absorbance change as a function of increasing pH. The inset depicts the ratio of two absorption peaks ($A_{418}/A_{623}$) as a function of temperature.
FIG. 5(B) depicts temperature dependent spectral changes of 1 v/v % of indicator 1 solution of 50 mM MOPS buffer containing 75% glycerol. The arrows indicate the direction of absorbance change as a function of decreasing temperature. The inset depicts the ratio of two absorption peaks ($A_{418}/A_{623}$) as a function of temperature.

Temperature dependence of the pH of MOPS buffer solution was studied. FIG. 5A shows the changes in the ratio of $A_{418}/A_{623}$ with the pH of the 50 mM MOPS buffer containing 75% glycerol. The ratio was linearly dependent on the pH of the solution (FIG. 5A inset). In order to examine the temperature effect of the pH, the same 50 mM MOPS buffer containing 75% glycerol was cooled down and the spectral changes were recorded (FIG. 5B). As the temperature of the solution is lower from room temperature to 170 K, the ratio of $A_{418}/A_{623}$ decreases from ~0.7 to ~0.25 (FIG. 5B inset). Lowering the temperature of the solution further to 85K did not cause any significant spectral changes. The ratio of $A_{418}/A_{623}$ at each temperature was converted to pH using the linear regression fit of the FIG. 5A inset. The resulting plot of the pH versus temperature is shown in FIG. 4. The pH of the MOPS buffer increased about 1.6 pH unit upon lowering the temperature of the solution from room temperature to ~170 K.

Figure 6:
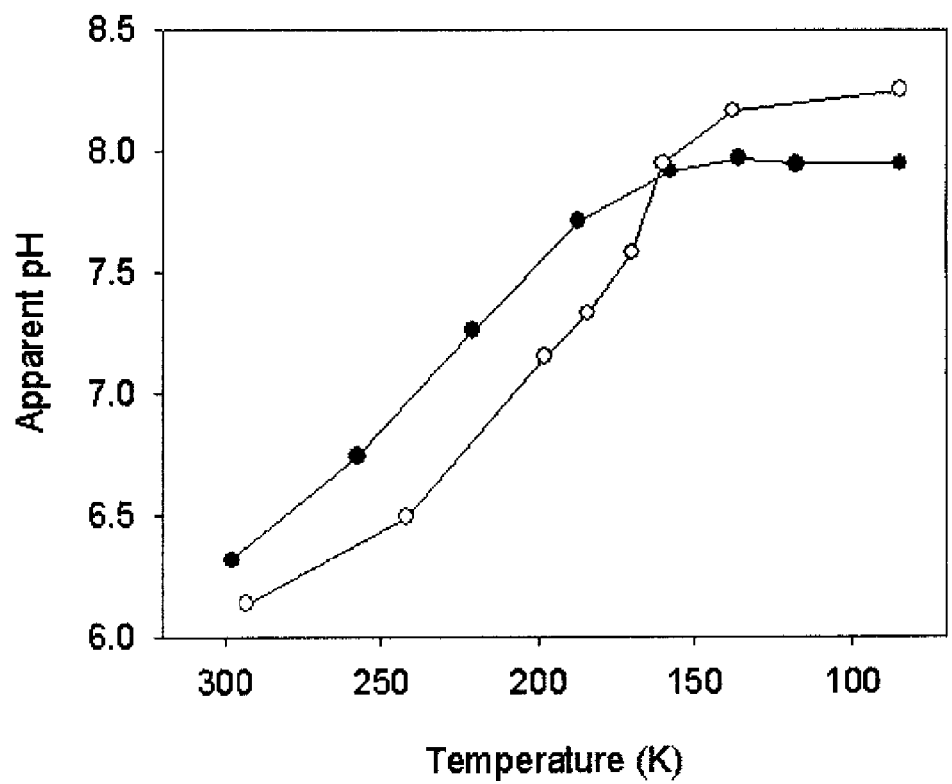
FIG. 6 depicts the temperature dependence of pH of MOPS buffer containing either 50% glycerol (○) or 75% glycerol (•)

Since glycerol is used in many biophysical studies performed at low temperature, the effect of the percentage of glycerol on the pH upon freezing was also investigated using MOPS buffer. The final concentration of the buffer was held constant but the amount of glycerol was varied from 75% to 50%. The results are shown in FIG. 6. As expected, a similar trend in pH was observed. However, the degree of change was somewhat larger for the sample containing 50% glycerol. Spectroscopy experiments with solutions containing glycerol concentrations less than 50% (vol/vol) were unsuccessful due to the difficulties of forming a transparent glass for optical spectrum measurements.

Example 6

Biophysical Measurements of Hemoglobin in a Temperature Resistant pH Buffer (HEPES:KPhosphate (60:40))

Lyophilized human hemoglobin (Sigma-Aldrich) was dissolved in 100 mM KPhosphate and centrifuged at $13.2 \times 10^3$ rpm to separated undissolved protein. The supernatant was then oxidized with 0.9 equiv $K_3Fe(CN)_6$. Excess oxidant was removed by passing the solution down a PD-10 column (GE Healthcare). The eluded protein was then concentrated using a microcentrifuge membrane (10,000 MWCO, Amicon) and stored at 4° C. until experimentation.

EPR spectra were recorded on a Bruker ESP 300 equipped with an Oxford liquid helium cryostat and an ITC4 temperature controller. Samples were prepared at room temperature by diluting the protein to a concentration of 0.40 mM with 100 mM buffer. All buffers contained 20 µM DTPA (diethylenetriaminepentaacetic acid) as a free iron chelating agent. Samples were flash frozen by repeatedly dipping in liquid $N_2$, followed by submersion and storage in liquid $N_2$ until analysis. The molar extinction coefficient of the Soret transition at 405 nm (179 $mM^{-1}$ $cm^{-1}$) for human methemoglobin was used to determine protein concentration. EPR parameters, where otherwise stated, were: $\nu$=9.058 GHz; microwave power: 20 db or 2 mW; T=25 K; number of scans=10; and scan rate=40 Gauss/sec.

Figure 7:
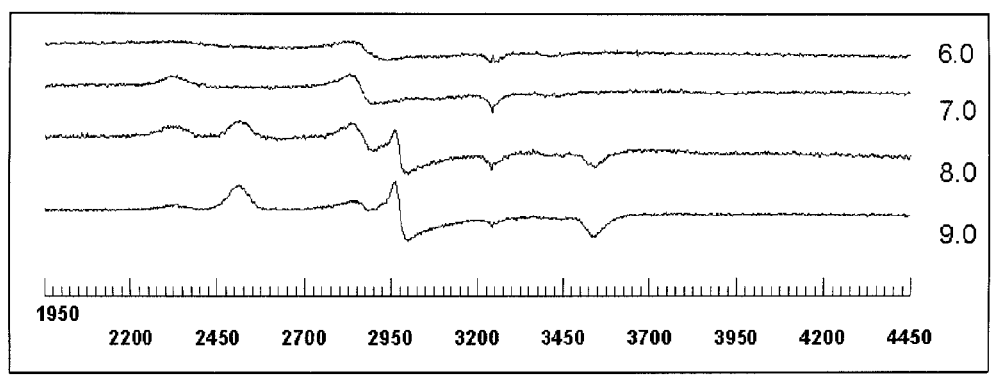
FIG. 7 depicts high field EPR spectra of methemoglobin (met-Hb) (400 μM) in 100 mM KPhosphate buffer at different initial pH's and 25 K.
Figure 8:
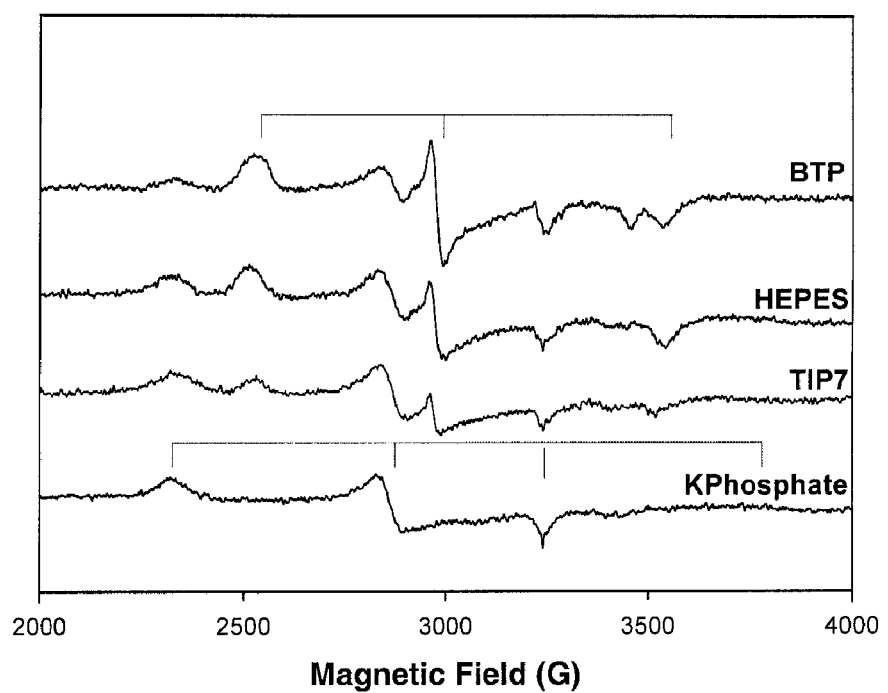
FIG. 8 depicts high field EPR spectra of met-Hb (400 μM) in 100 mM various buffers (BTP; HEPES; KPhosphate; and HEPES:KPhosphate (60:40) (TIP7)) at pH 7.0 and 25 K.

The high field EPR spectra of met-Hb in phosphate at 25K at various pH values (measured at room temperature) are shown in FIG. 7. The pH dependent low spin transition from iron with no water bound (LS2) to hydroxy-bound iron (LS3) is clearly evidenced by increasing intensity of peaks with g-factors 2.57, 2.17, and 1.82 with increasing pH from 7.0 to 9.0 units. FIG. 8 depicts the high field (low spin) EPR spectra for met-Hb in KPhosphate, HEPES:KPhosphate (60:40), and BTP buffers, all of which were measured pH 7.0 at room temperature before and after spectra were recorded. All three spectra were different, and represent different ratios of the three spin states (LS1, LS2, LS3). The spectrum of HEPES: KPhosphate (60:40) shows spin states intermediate of those shown in the presence of KPhosphate or HEPES buffers. The HEPES:KPhosphate (60:40) spectrum most closely resembles the spectrum of pH 8 KPhosphate. This result supports data obtained using indicator 1, which shows KPhosphate buffer to have a pH change of ~-0.7 units when starting from pH 8.0 (FIG. 3). Since the EPR data for human met-Hb is in accordance with the results obtained using indicator dyes, the EPR spectrum of met-Hb obtained in the presence of the HEPES:KPhosphate (60:40) buffer at 25 K may reflect a truer representation of distribution of iron spin states at pH 7.0 and at physiological temperature than the corresponding spectra for protein suspended in KPhosphate, HEPES, or BTP buffers.

Data Processing

For the indicator dyes, a plot of the ratio of two wavelength maxima (around 420 and 620 nm) vs pH was obtained for each buffer. This plot was fit to either a linear or non-linear regression curve to best fit the experimental data. Then, absorbance ratio for the same two peaks recorded at low temperature was converted to 'pH' using the calibration curve. The term 'pH' that used in the text represents the physical quantity that is correlated with the activity of proton in the water-glycerol mixture in liquid or solid phase.

Example 7

A Temperature Resistant pH Buffer for an Antibiotic Formulation

The following experiment was done to determine whether a storage-stable antibiotic formulation could be prepared with a temperature resistant pH buffer. Oxacillin, a penicillin analog, is most stable at a pH of 6.0-6.5. Solutions of oxacillin (200 µM) were prepared at 277 K in the presence of various buffers at pH 7.0: KPhosphate, HEPES, BisTris Propane, and HEPES:KPhosphate (60:40). Aliquots of these solutions were subjected to various freeze-thaw regiments and the extent of degradation of the antibiotic was monitored quantitatively over several days using HPLC. Control solutions of oxacillin at 293 K and at 277 K in the presence of mixtures of all buffers demonstrated that the freeze-thaw process, rather than the presence of certain buffer molecules, accounted for the observed degradation over time. All buffered solutions measured pH 7.0 at room temperature before and after experimentation.

Figure 9:
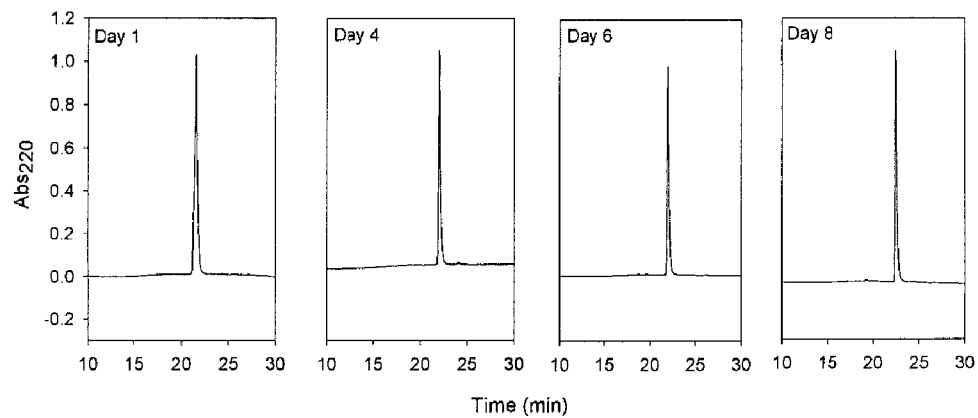
FIG. 9 depicts representative HPLC chromatograms of oxacillin (200 μM) solutions containing either 50 mM HEPES:KPhosphate (60:40) buffer (A) or 50 mM BisTris Propane buffer (B) when stored at 193 K over the course of eight days.
Figure 9:
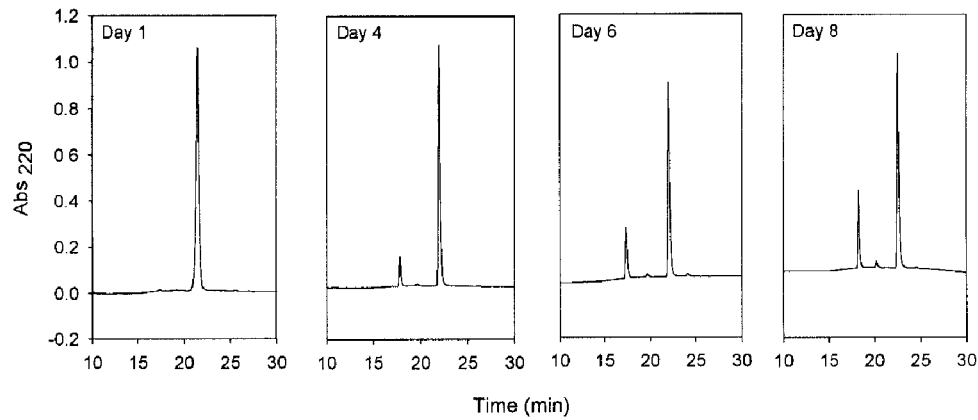

The antibiotic solutions were placed in a storage freezer with a temperature of 193 K. Over the course of eight days, each sample was thawed to remove an aliquot for HPLC analysis, and the remainder of each sample was subsequently returned to frozen storage. FIG. 9 depicts representative chromatograms that illustrates the extent of degradation of oxacillin ($T_r$=22.5 min) to its hydrolysis product ($T_r$=17.8 min) in the presence of 50 mM HEPES:KPhosphate (60:40) buffer (FIG. 9A) and 50 mM BisTris Propane buffer (FIG. 9B). The antibiotic stored in the BisTris Propane buffered solution showed greater hydrolysis than the antibiotic stored in the HEPES:KPhosphate (60:40) buffered solution. Thus, the pH-induced hydrolysis of oxacillin which occurs under freeze-thaw storage conditions is reduced when oxacillin is stored in a solution containing a temperature resistant pH buffer, such as HEPES:KPhosphate (60:40).

Example 8

Derivation of a Set of Universal Temperature Resistant pH Buffer Standards (Prophetic Example)

A set of temperature resistant pH buffers that span the biochemically and physiologically useful pH values will be prepared. A buffer having a positive temperature coefficient is selected from the group of tartrate, phosphate, and borate, and combined with a buffer having a negative temperature coefficient selected from the group of phthalate, acetate, MES, MOPS, HEPES, TRIS, BisTris, and BisTris Propane. The suitable buffer systems that span this range and which may be configured as a temperature independent buffer system are exemplified in Table 5.

TABLE 5

Temperature resistant pH buffer systems over a defined pH range

| | Buffers with −ΔpH/dT | | | | | |
|---|---|---|---|---|---|---|
| Buffers with +ΔpH/dT | Phthalate (2.95, 5.41) | Acetate (4.76) | MES (6.1) | MOPS (7.14) | TRIS (8.06) | BisTrisPropane (6.8, 9.0) |
| Tartrate (3.00, 4.40)[1] | Tartrate-Phthalate (pH 2.3–6.0) | Tartrate-Acetate (pH 3.5–5.6) | | | | |
| Phosphate (2.95, 7.20, 12.33) | Phosphate-Phthalate (pH 2.0–3.8; pH 4.5–7.7) | | MES-Phosphate (pH 5.2–8.1) | MOPS-Phosphate (pH 6.1–8.2) | TRIS-Phosphate (pH 6.5–9.0) | BisTrisPropane-Phosphate (pH 5.9–8.1) |
| Borate (9.23, 12.71, 13.80) | | | | | TRIS-Borate (pH 7.2–10) | BisTrisPropane-Borate (pH 8.3–10) |

[1]Values shown in parentheses indicate pKa values for the single buffers.

A series of 50 mM buffer solutions will be prepared that include different combinations of concentrations for each buffer pair having opposite temperature coefficients. The temperature dependence of pH for each buffer composition will be examined as described in Example 5. The buffer composition for each buffer pair that provides the smallest change of pH as a function of temperature will be selected for each desired temperature range of interest.

Example 9

Ascertaining the Buffering Capacity of a Temperature Resistant pH Buffer System (Prophetic Example)

The following experiment is performed to determine the buffering capacity of a temperature resistant pH buffer system. A series of solutions is prepared that contain 50 mM of the HEPES:KPhosphate (60:40) buffer system (pH 7.0, measured at room temperature), 1% indicator 1 (wt/vol) and 75% glycerol (vol/vol)). Hydrochloric acid (HCl) or potassium hydroxide (KOH) is added incrementally to a subset of the solutions to achieve 25 mM (0.50 equivalent), 50 mM (1.0 equivalent), 75 mM (1.5 equivalents) and 100 mM (2.0 equivalents) of the acid or base in a solution. Potassium chloride (KCl) is added as necessary to maintain constant ionic strength between the solutions. A complete solution containing KCl, but lacking HCl or KOH, is prepared and serves as the control for evaluating the ΔpH as a function of added acid or base. The solutions are equilibrated at identical temperatures spanning the temperature range of 298 K to 90 K, and the ratiometric and calorimetric analysis of indicator 1 is performed in a manner similar to that described in Example 5. The buffering capacity, β, is determined as the amount of acid or base (equivalents) needed to change the pH of the solution by one pH-unit. The β values may be plotted as a function of temperature to evaluate the temperature dependence of buffering capacity.

Example 10

Evaluating Temperature Resistant pH Buffers as Physiologically Acceptable Buffers for Anthracycline Glycoside Formulations (Prophetic Example)

Anthracycline glycosides are antitumor agents that undergo pH-dependent and temperature-dependent hydrolysis. An exemplary anthracycline aminoglycoside used for chemotherapy is doxorubicin hydrochloride (ADRIAMYCIN™ (Adria Laboratories; Dublin, Ohio). The optimum pH range for storage stable (at 4-8° C.), ready-to-use formulations of doxorubicin is pH 3.0. Doxorubicin gradually reduces therapeutic activity upon repeated freeze (−20° C.)-thaw (+37° C.) treatments, which correlates with the hydrolysis of the aminoglycoside bond in the compound.

The following experiment is performed to evaluate the suitability of a temperature resistant pH buffer for doxorubicin hydrochloride formulations stored under frozen conditions. Methods for evaluating doxorubicin stability as a function of formulation conditions are well-established. A stability indicating assay based upon HPLC analysis of doxorubicin is used in conjunction with a modification of the accelerated stability assays of Gatti et al. (2000).

Lyophilized powders of doxorubicin hydrochloride will be dissolved in solutions that contain 50 mM of HEPES, 50 mM KPhosphate, or 50 mM HEPES/KPhosphate (60:40). Each solution contains doxorubicin hydrochloride at 1 mg/ml and displays a pH of 7.0 (measured at room temperature). The solutions are de-aerated by nitrogen bubbling and sterilized by filtration through 0.22 mm microporous membranes under nitrogen pressure prior to storage. An aliquot of each solution is subjected to HPLC analysis, and the initial concentration of doxorubicin for each solution is determined using a standard calibration curve developed from doxorubicin solutions of known concentration. The samples are subjected to repeated daily cycles of freeze (−20° C.)-thaw (+37° C.) treatment over the course of 90 days. After each thawing, an aliquot of each solution is subjected to HPLC analysis. The concentration of intact doxorubicin hydrochloride remaining after each freeze-thaw treatment is determined as described above and plotted as a function of freeze-thaw cycle (or time, such as days).

Example 11

Preparing a Temperature Resistant Solution for Stabilizing Thrombin-Activated Porcine Factor VIII (Prophetic Example)

The thrombin-activated porcine factor VIII (fvIIIa) is a stable, active, heterotrimer at pH 6.0 at 4° C. or 20° C.; however, this protein undergoes a sharp decline in coagulation activity between pH 7 and 8. The loss of activity correlates with pH-induced dissociation and precipitation of individual subunits of the trimeric protein.

The following experiments will be performed to demonstrate that conventional buffered solutions adjusted to pH 6.0 are unsuitable for preparing solutions of fVIIIa for low temperature storage (180 K). Solutions containing 50 mM MOPS (pH 6.1), 75% glycerol, $4 \times 10^{-7}$ M fVIIIa (0.05 mg/mL protein), and optionally, 1% indicator 1 are prepared. The solutions are adjusted to pH 6.1 at room temperature (293 K). Aliquots of the solutions are equilibrated at 180 K and 293 K for two hours. The ratiometric calorimetric analysis of solutions containing indicator 1 is performed for purposes of determining solution pH at the two temperatures. The solutions lacking indicator 1 are then equilibrated at room temperature for one hour, and the coagulation activity assays are performed as described by Lollar and Parker (1990). The MOPS buffered solution stored at 180 K should undergo an increase in pH to ~pH 7.7, whereas the MOPS buffered solution stored at 293 K should remain at pH 6.1 (FIG. 6). Consequently, and in accordance with Lollar and Parker (1990), the coagulation activity fVIIIa should decline in the solution following its storage at low temperature.

The following experiment is performed to identify a temperature resistant pH solution compatible with maintaining the activity of fVIIIa after storage at low temperatures. A buffer system comprising MOPS and KPhosphate displays a solution pH range from 6.1 to 8.2 (Table 5; Example 7). A series of 50 mM solutions are prepared that contain different concentration ratios of MOPS and KPhosphate in accordance with Example 7. The pH of the solutions is adjusted to pH 6.1 at 293 K. The temperature dependence of pH for each buffer composition will be examined as described in Example 5, particularly for the range spanning 180 K and 293 K. The buffer composition of MOPS and KPhosphate that provides a $\Delta pH(180\ K, 293\ K) \leq 0.7$ pH-unit will be selected as the candidate storage buffer for fVIIIa, because this solution is not expected to exceed pH 6.8 upon cooling to 180 K. The fVIIIa protein stored in this solution should remain stable upon cooling to this low temperature, because the protein remains stable at pH values less than 7 (Lollar and Parker 1990).

Protein solutions containing the identified MOPS-KPhosphate buffer system will be prepared and evaluated in a manner similar to the protein solutions containing MOPS alone. One expects that fVIIIa stored in the MOPS-KPhosphate solution will retain nearly full coagulation activity following thawing from storage at 180 K.

REFERENCES

1. Alam, A. S. et al., "LIQUID CISPLATIN FORMULATIONS", U.S. Pat. No. 4,915,956 (Apr. 10, 1990).
2. Bates, R. G, et al., "Dissociation Constants of Acetic Acid and Primary Phosphate Ion and Standards for pH in 10, 20, and 40 wt % Ethanol/Water Solvents at 25, 0, −5, and −10 "C", Analytical Chemistry, 52, 1598-1601, 1980.
3. Biological Buffers at http://www.sigmaaldrich.com/Brands/Fluka_Riedel_Home/Bioscience/BioChemika_Ultra/Biological_Buffers.html (2006).
4. Chilson, O. P. et al., "Effects Of Freezing On Enzymes", Federation proceedings 24, pp. S55-65, March-April 1965.
5. Dawson, R M C, et al. "Data For Biochemical Research", $3^{rd}$ ed., p. 421, Clarendon Press, Oxford, 1986.
6. Gatti, G. et al., "INJECTABLE READY-TO-USE SOLUTIONS CONTAINING AN ANTITUMOR ANTHRACYCLINE GLYCOSIDE", U.S. Pat. No. 6,107,285 (Aug. 22, 2000).
7. Goldberg, N. et al., "Thermodynamic Quantities for the Ionization Reactions of Buffers", Journal of Physical and Chemical Reference Data, 31, pp. 231, June, 2002.
8. Good, N. E. et al., "Hydrogen ion buffers for biological research", Biochemistry, 5, pp. 467-77, February, 1966.
9. Good, N. E. et al., "Hydrogen ion buffers", Methods Enzymol. 24, pp. 53-68, 1972.
10. Hafeman, D. G. et al., "Fundamental thermochromic properties of buffered pH indicator solutions and the formation of "athermochromic" systems" J. Phys. Chem. 97:3058-66 (1993)
11. Hui Bon Hoa, G. et al., "Ionic strength and protonic activity of supercooled solutions used in experiments with enzyme systems", J. Biol. Chem, 248, pp. 4649-54, Jul. 10, 1973.
12. Lollar, P. et al., "pH-dependent Denaturation of Thrombin-activated Porcine Factor VIII," J. Biol. Chem., 265, pp. 1688-92, Jan. 25, 1990.
13. Michelson, S. C., "Dielectric properties of supercooled cryoprotectant agents", Physics in Medicine & Biology, 41, pp. 2053-66, October, 1996.
14. Orii, Y. et al., "Measurement of the pH of frozen buffer solutions by using pH indicators", J. Biochem (Tokyo), 81, pp. 163-8, January 1977.
15. Reichardt, C. "Solvents and Solvent Effects in Organic Chemistry", Wiley-VCH, Weinheim, Germany, ed. 3rd, 653 pages, 2003.
16. Svistunenko D. A., et al., "The pH dependence of naturally occurring low-spin forms of methaemoglobin and metmyoglobin: an EPR study", Biochemical Journal, 351, pp. 595-504, Nov. 1, 2000.
17. Travers, F. et al., "Dielectric constants of alcoholic-water mixtures at low temperature", Journal of Physical Chemistry 74, pp. 2243-44, 1970.
18. Van den Berg, L. et al., "Effect of freezing on the pH and composition of sodium and potassium phosphate solutions; the reciprocal system KH2PO4-Na2-HPO4-H2O", Archives of biochemistry and biophysics, 81, pp. 319-329, April, 1959.
19. Van den Berg, L., "Composition and ph changes during freezing of solutions containing calcium and magnesium phosphate", Cryobiology, 6, 10-4, July-August, 1969.
20. Williams-Smith, D. L. et al., "Changes in apparent pH on freezing aqueous buffer solutions and their relevance to biochemical electron-paramagnetic-resonance spectroscopy", Biochem. J., 167, pp. 593-600, Dec. 1, 1977.

What is claimed is:

1. A composition made by a method comprising:
    selecting a pH of the composition, the composition having a pH of 6 to 8;
    selecting a first buffer with a negative temperature coefficient, the first buffer comprising HEPES or BisTrisPropane;
    selecting a second buffer with a positive temperature coefficient, the second buffer comprising potassium phosphate; and
    forming the composition comprising the first buffer and the second buffer;
    wherein the composition does not comprise a pH-indicator dye,
    the composition has an average temperature coefficient $\Delta pH/\Delta T(T_a, T_b) \leq 1 \times 10^{-3}$ pH-unit/K for $T_a = 253$ K and $T_b = 273$ K, or $T_a = 273$ K and $T_b = 293$ K and
    the HEPES or BisTrisPropane comprises 25-60 mole percent of the sum of the first and second buffers, and potassium phosphate comprises the remainder mole percent of the sum of the first and second buffers.

2. A solution, comprising:

a first buffer with a negative temperature coefficient, the first buffer comprising phthalate, acetate, MOPS, Tris, BisTris, BisTrisPropane, HEPES or MES; and a second buffer with a positive temperature coefficient, the second buffer comprising tartrate, phosphate, or borate;

wherein the solution has an average temperature coefficient $\Delta pH/\Delta T(T_a,T_b) \leq 1 \times 10^{-3}$ pH-unit/K for $T_a=4$ K and $T_b=313$ K, and wherein the solution does not comprise a pH-indicator dye.

3. A buffer system, comprising:

a first buffer with a positive temperature coefficient; and a second buffer with a negative temperature coefficient;

wherein the buffer system has an average temperature coefficient $\Delta pH/\Delta T(T_a,T_b) \leq 1 \times 10^{-3}$ pH-unit/K for $T_a=4$ K and $T_b=313$ K, a $\Delta pH(4\ K, 313\ K) \leq 0.31$ pH-unit, and a buffering capacity of at least 0.01 for the temperature range of 4 K to 313 K, wherein the buffer system does not comprise a pH-indicator dye, and the buffer system has a buffer concentration of 25 mM to 75 mM.

4. The solution of claim 2, wherein the solution has a $\Delta pH(T_a, T_b)$ value selected from the group consisting of $\Delta pH(253\ K, 273\ K) \leq 0.02$ pH-unit;

$\Delta pH(273\ K, 293\ K) \leq 0.02$ pH-unit; $\Delta pH(253\ K, 293\ K) \leq 0.04$ pH-unit;

$\Delta pH(273\ K, 293\ K) \leq 0.04$ pH-unit; $\Delta pH(253\ K, 313\ K) \leq 0.06$ pH-unit;

$\Delta pH(203\ K, 313\ K) \leq 0.11$ pH-unit; $\Delta pH(193\ K, 313\ K) \leq 0.12$ pH-unit;

$\Delta pH(143\ K, 313\ K) \leq 0.17$ pH-unit; $\Delta pH(90\ K, 313\ K) \leq 0.22$ pH-unit and $\Delta pH(4\ K, 313\ K) \leq 0.31$ pH-unit.

5. The solution of claim 2, wherein the first buffer and the second buffer comprise physiologically acceptable buffers.

6. The solution of claim 5, wherein the solution has a pH within the range from 3 to 10.

7. The solution of claim 6, wherein the solution has a buffer capacity of at least 0.01.

8. The solution of claim 6, wherein the solution has a buffer capacity within the range of 0.01 to 10.

9. The buffer system of claim 3, wherein the buffer system has an average temperature coefficient $\Delta pH/\Delta T(T_a,T_b)$ of $1.0 \times 10^{-5}$ pH-unit/K to $1.0 \times 10^{-3}$ pH-unit/K for $T_a=4$ K and $T_b=313$ K.

10. The buffer system of claim 3, wherein the first and second buffers comprise physiologically acceptable buffers.

11. The buffer system of claim 10, wherein the buffer system has buffering capacity within a pH range from 3 to 10.

12. The buffer system of claim 11, having a $\Delta pH(253\ K, 293\ K) \leq 0.04$ pH-unit.

13. The composition of claim 1, having a $\Delta pH(170\ K, 298\ K) \leq 0.03$ pH-unit.

14. The buffer system of claim 3, having a $\Delta pH(170\ K, 298\ K) \leq 0.03$ pH-unit.

15. The composition of claim 1, having a buffer concentration of 25 mM to 75 mM.

* * * * *

UNITED STATES PATENT AND TRADEMARK OFFICE
CERTIFICATE OF CORRECTION

PATENT NO.         : 8,183,046 B2                                               Page 1 of 1
APPLICATION NO.    : 11/622098
DATED              : May 22, 2012
INVENTOR(S)        : Yi Lu et al.

It is certified that error appears in the above-identified patent and that said Letters Patent is hereby corrected as shown below:

In column 5, line 65, the word "calorimetric" should read --colorimetric--.

In column 8, line 49, the words "of 0.34 pH-unit." should read --of ~ 0.34 pH-unit.--.

In column 15, line 52, the word "calorimetric" should read --colorimetric--.

Signed and Sealed this
Twenty-second Day of January, 2013

David J. Kappos
*Director of the United States Patent and Trademark Office*